US009789221B2

(12) United States Patent
Dieck et al.

(10) Patent No.: US 9,789,221 B2
(45) Date of Patent: *Oct. 17, 2017

(54) BIOCOMPATIBLE PHASE INVERTIBLE PROTEINACEOUS COMPOSITIONS AND METHODS FOR MAKING AND USING THE SAME

(71) Applicant: Tenaxis Medical, Inc., Mountain View, CA (US)

(72) Inventors: Ronald Dieck, Palo Alto, CA (US); Ian J. Handley, Mountain View, CA (US); Neil Winterbottom, San Mateo, CA (US); Joanna Wong, Santa Clara, CA (US)

(73) Assignee: Mallinckrodt Pharma IP Trading D.A.C., Dublin (IE)

( * ) Notice: Subject to any disclaimer, the term of this patent is extended or adjusted under 35 U.S.C. 154(b) by 82 days.

This patent is subject to a terminal disclaimer.

(21) Appl. No.: 14/178,086

(22) Filed: Feb. 11, 2014

(65) Prior Publication Data

US 2014/0235825 A1 Aug. 21, 2014

Related U.S. Application Data

(63) Continuation of application No. 14/055,712, filed on Oct. 16, 2013, which is a continuation of application No. 13/471,746, filed on May 15, 2012, now Pat. No. 8,586,671, which is a continuation of application No. 12/326,835, filed on Dec. 2, 2008, now Pat. No. 8,198,363.

(60) Provisional application No. 60/991,867, filed on Dec. 3, 2007.

(51) Int. Cl.
| | |
|---|---|
| *C08G 63/48* | (2006.01) |
| *A61L 24/10* | (2006.01) |
| *A61L 24/04* | (2006.01) |
| *A61L 31/04* | (2006.01) |

(52) U.S. Cl.
CPC ........... *A61L 24/108* (2013.01); *A61L 24/043* (2013.01); *A61L 24/10* (2013.01); *A61L 31/041* (2013.01)

(58) Field of Classification Search
CPC ................................ A61K 47/42; C08G 63/48
USPC ...................................................... 525/54.1
See application file for complete search history.

(56) References Cited

U.S. PATENT DOCUMENTS

| | | | |
|---|---|---|---|
| 3,438,374 A | 4/1969 | Falb et al. | |
| 4,448,718 A * | 5/1984 | Yannas ................. | A61L 15/225 106/135.1 |
| 5,092,841 A | 3/1992 | Spears | |
| 5,292,362 A | 3/1994 | Bass et al. | |
| 5,385,606 A | 1/1995 | Kowanko | |
| 5,575,815 A | 11/1996 | Slepian et al. | |
| 5,583,114 A | 12/1996 | Barrows et al. | |
| 5,843,156 A | 12/1998 | Slepian et al. | |
| 6,162,241 A | 12/2000 | Coury et al. | |
| 6,290,729 B1 | 9/2001 | Slepian et al. | |
| 6,302,898 B1 | 10/2001 | Edwards et al. | |
| 6,310,036 B1 | 10/2001 | Browdie | |
| 6,329,337 B1 | 12/2001 | Morita et al. | |
| 6,371,975 B2 | 4/2002 | Cruise et al. | |
| 6,372,229 B1 | 4/2002 | Ollerenshaw et al. | |
| 6,423,333 B1 | 7/2002 | Stedronsky et al. | |
| 6,458,147 B1 | 10/2002 | Cruise et al. | |
| 6,475,182 B1 | 11/2002 | Hnojewyj et al. | |
| 6,547,806 B1 | 4/2003 | Ding | |
| 7,303,757 B2 | 12/2007 | Schankereli et al. | |
| 8,198,363 B2 | 6/2012 | Dieck et al. | |
| 8,586,671 B2 | 11/2013 | Dieck et al. | |
| 2002/0015724 A1 | 2/2002 | Yang et al. | |
| 2002/0019490 A1 | 2/2002 | Maugans et al. | |
| 2002/0022588 A1 | 2/2002 | Wilkie et al. | |
| 2002/0032143 A1 | 3/2002 | Wei et al. | |
| 2002/0133193 A1 | 9/2002 | Ginn et al. | |
| 2002/0173770 A1 | 11/2002 | Flory et al. | |
| 2002/0183244 A1 | 12/2002 | Ollerenshaw et al. | |
| 2004/0052850 A1 | 3/2004 | Schankereli | |
| 2004/0081676 A1* | 4/2004 | Schankereli ......... | A61K 9/0024 424/401 |
| 2009/0143500 A1 | 6/2009 | Dieck et al. | |
| 2012/0222584 A1 | 9/2012 | Dieck et al. | |
| 2014/0041547 A1 | 2/2014 | Dieck et al. | |

FOREIGN PATENT DOCUMENTS

JP 2000-503883 4/2010

OTHER PUBLICATIONS

Burg et al., In Irradiation of Polymers; Clough, R., et al.; ACS Symposium Series; American Chemical Society; Washington, DC 1996.*
European search report and search opinion dated Jan. 4, 2013 for EP Application No. 08856256.
International search report and written opinion dated Feb. 4, 2009 for PCT/US208/085283.
Office action dated Mar. 26, 2013 for U.S. Appl. No. 13/471,746.
Office action dated Mar. 29, 2010 for U.S. Appl. No. 12/326,835.
Office action dated Mar. 31, 2011 for U.S. Appl. No. 12/326,835.

(Continued)

*Primary Examiner* — Yong Chu
*Assistant Examiner* — Sonya Wright

(57) ABSTRACT

Biocompatible phase invertible proteinaceous compositions and methods for making and using the same are provided. Phase invertible compositions in accordance with the invention are prepared by combining a liquid proteinaceous substrate and a liquid crosslinking composition, where the liquid crosslinking composition includes a macromolecular crosslinking agent. Also provided are kits for use in preparing the subject compositions. The subject compositions, kits and systems find use in a variety of different applications.

9 Claims, 1 Drawing Sheet

(56) References Cited

OTHER PUBLICATIONS

Office action dated Jul. 3, 2012 for U.S. Appl. No. 13/471,746.
Office action dated Oct. 6, 2009 for U.S. Appl. No. 12/326,835.
Office action dated Oct. 18, 2010 for U.S. Appl. No. 12/326,835.
Roberts, et al. Chemistry for peptide and protein PEGylation. Adv Drug Deliv Rev. Jun. 17, 2002;54(4):459-76.

\* cited by examiner

| Lot# | Cure Time | Viscosity (cm) | Viscosity Index | Adhesion | Peel | Burst (mmHg) | Elasticity | Elasticity Distance (cm) | Flexibility |
|---|---|---|---|---|---|---|---|---|---|
| 004-49 | 19 | 19.5 | 1.00 | V. Good + | V. Difficult + | 549.0 | 1.0-2.1 | 1.1 | Excellent |
| 004-49 | 20 | 18.7 | 0.96 | V. Good + | V. Difficult + | 581.4 | 1.0-2.0 | 1.0 | Excellent |
| Mean | 19.50 | 19.1 | 0.98 | | | 565.2 | | 1.1 | |
| 004-42-1 | 21 | 21.0 | 0.95 | Medium | Difficult | 353.1 | 1.0-3.1 | 2.1 | Excellent |
| 004-42-1 | 23 | 23.6 | 1.07 | V. Good | V. Difficult | 354.3 | 1.0-2.5 | 1.5 | Excellent |
| Mean | 22.00 | 22.3 | 1.01 | | | 353.7 | | 1.8 | |
| 004-42-2 | 13 | 14.1 | 1.04 | Good | Difficult | 538.1 | 1.0-1.8 | 0.8 | Excellent |
| 004-42-2 | 14 | 14.8 | 1.10 | V. Good | Difficult | 594.3 | 1.0-1.9 | 0.9 | Good |
| Mean | 13.50 | 14.5 | 1.07 | | | 566.2 | | 0.9 | |
| 004-42-3 | 36 | >42 | >1.22 | Medium | Difficult | 270.5 | 1.0-2.0 | 1.0 | Excellent |
| 004-42-3 | 31 | >42 | >1.22 | Good | Difficult | 221.9 | 1.0-1.8 | 0.8 | Excellent |
| Mean | 33.50 | | | | | 246.2 | | 0.9 | |
| 003-118-2 | 11 | 21.8 | 1.90 | V. Good | V. Difficult | 432.6 | 1.0-1.9 | 0.9 | Excellent |
| 003-118-2 | 12 | 20.1 | 1.75 | Good | V. Difficult | 565.8 | 1.0-1.8 | 0.8 | Excellent |
| Mean | 11.50 | 21.0 | 1.82 | | | 499.2 | | 0.9 | |

| Lot# | Comments |
|---|---|
| 004-49 | Yellow |
| 004-49 | Yellow |
| 004-42-1 | Creamy yellow; thin film on aorta |
| 004-42-1 | Creamy yellow |
| 004-42-2 | Creamy yellow; no burst occur |
| 004-42-2 | Creamy yellow |
| 004-42-3 | Clear yellow; let cure for 2 min; thin film on aorta |
| 004-42-3 | Clear yellow; let cure for 2 min; thin film on aorta; sample ran underneath collar, very little on aorta |
| 003-118-2 | Milky |
| 003-118-2 | Milky |

BIOCOMPATIBLE PHASE INVERTIBLE PROTEINACEOUS COMPOSITIONS AND METHODS FOR MAKING AND USING THE SAME

CROSS-REFERENCE TO RELATED APPLICATION

This application is a continuation of U.S. patent application Ser. No. 14/055,712, filed Oct. 16, 2013, which is a continuation of U.S. patent application Ser. No. 13/471,746, (now U.S. Pat. No. 8,586,671), filed May 15, 2012, which is a continuation of U.S. patent application Ser. No. 12/326,835, (now U.S. Pat. No. 8,198,363), filed Dec. 2, 2008, which claims priority to U.S. Provisional Patent Application No. 60/991,867, filed Dec. 3, 2007; the full disclosures of which application are herein incorporated by reference.

INTRODUCTION

A number of sealant compositions have become available to control fluid leakage at a surgical site, as well as for other applications. However, currently available sealant compositions may suffer from serious limitations with regards to the field in which they can be used, as well as their biocompatibility and their physical properties. Side effects, such as inflammation, acute fibrous formation at the wound site, toxicity, inability to be used in a bloody field, poor physical properties of the sealant, and poor adhesion to the surgical site, may have a serious impact on the patient and resultantly may play a significant role in the long term efficacy of the repair. Further, useful sealants have properties that can render them more effective for surgical application. Characteristics, such as the ability to be localized to a specific location, adequately long or short polymerization times, and adequate in vivo resorption characteristics, are vital to a successful completion of the sealing procedure.

As such, there is a continued need for the development of new biocompatible compositions for use as sealants, as well as for use in other applications.

SUMMARY

Biocompatible phase invertible proteinaceous compositions and methods for making and using the same are provided. Phase invertible compositions in accordance with aspects of the invention are prepared by combining a liquid proteinaceous substrate and a liquid crosslinking component, where the liquid crosslinking component includes a macromolecular crosslinking agent.

The macromolecular crosslinking agent is produced by combining an excess of a crosslinking agent, e.g., a heat-treated dialdehyde, with an amount of a physiologically acceptable polymer, such as a glycosaminoglycan. The excess of crosslinking agent and physiologically acceptable polymer react to produce a macromolecular crosslinking agent. Upon combination of the macromolecular crosslinking agent with the proteinaceous substrate, the macromolecular crosslinking agent reacts with proteins in the substrate component to produce a final composition characterized by the presence of an interpenetrating network.

Also provided are kits for use in preparing the subject compositions. The subject compositions, kits and systems find use in a variety of different applications.

BRIEF DESCRIPTION OF THE FIGURE

FIG. 1 provides a table of results observed with different sealant compositions, as described in the Experimental Section, below.

DETAILED DESCRIPTION

Biocompatible phase invertible proteinaceous compositions and methods for making and using the same are provided. The subject phase invertible compositions are prepared by combining a liquid proteinaceous substrate and a liquid crosslinking composition, where the liquid crosslinking composition includes a macromolecular crosslinking agent. Also provided are kits for use in preparing the subject compositions. The subject compositions, kits and systems find use in a variety of different applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, phase invertible compositions in accordance with the invention are described first in greater detail, followed by a review of applications in which the compositions find use, as well as a review of kits and systems that find use in making or using the subject phase invertible compositions.

Biocompatible Phase Invertible Proteinaceous Composition

As summarized above, the subject invention provides a biocompatible phase invertible proteinaceous composition. The composition is one that, over time, undergoes a phase inversion from a first, liquid state to a second, solid state. In the first, liquid state, the phase invertible composition has a viscosity sufficient such that it can be caused to flow through a medical canula or sprayed onto a target tissue site. The phase invertible compositions are characterized by being capable of bonding tissue in both wet (e.g., blood) and dry environments, where adhesion of the composition to the tissue is exceptionally strong. An aspect of the compositions is that, once they are applied to a target tissue location, they remain at the target tissue location. A further aspect of the subject compositions is that they are well-tolerated by the body and do not elicit a substantial, if any, inflammatory response.

The subject phase invertible proteinaceous compositions are prepared by combining or mixing a liquid proteinaceous substrate with a liquid crosslinking composition. Each of these precursor components or compositions is now reviewed separately in greater detail.

Crosslinker Composition

As indicated above, the phase invertible composition is produced by combining a liquid proteinaceous substrate, as described above, with a liquid crosslinker composition that includes a macromolecular crosslinking agent. While the viscosity of the crosslinking component may vary, in certain embodiments it approximates the viscosity of the proteinaceous component, expressed in centistokes (cSt) at about 25° C., ranging from 10 cSt to 150 cSt, such as 30 cSt to 70 cSt. The crosslinking component may be sterilized according to any convenient protocol, where sterilization protocols of interest include, but are not limited to: gamma, electron beam, and the like. The liquid crosslinking component is one that is storage stable. By storage stable is meant that the substrate may be maintained under storage conditions, such as room temperature for a period of time of at least 1 years or longer, such as 3 years or longer, without undergoing any substantial change that negatively impacts the function of the substrate such that it is no longer suitable for use in preparing a biocompatible phase invertible composition of the invention.

The crosslinking component is one that is produced by combining an excess of a crosslinking agent with an amount of a physiologically acceptable polymer. Examples of crosslinking agents include, but are not limited to: photo-oxidative molecules; carbodimides; carbonyl containing compounds, e.g., mono- and dicarbonyls, including carboxilic acids, e.g., dicarboxylic acids, such as adipic acid, glutaric acid and the like, and aldehydes, including mono- and dialdehydes, e.g. glutaraldehyde; etc. In certain embodiments, the crosslinker employed is an aldehyde crosslinker. In certain of these embodiments, the aldehyde crosslinker is pretreated to produce a stabilized aldehyde crosslinker, for example, a stabilized glutarhaldehyde crosslinker, e.g., where the crosslinker is heat stabilized aldehyde, such as heat stabilized glutaraldehyde (such as described in U.S. Pat. No. 7,303,757, the disclosure of which is herein incorporated by reference).

While the amount of crosslinking agent in the composition may vary, in certain embodiments the amount of crosslinking agent ranges from 0.1 to 20% (v/v), such as 0.5 to 15% (v/v) and including 1 to 10% (v/v).

In addition to the cross-linking agent, the crosslinking composition further includes an amount of a physiologically acceptable polymer. The physiologically acceptable polymer may be any polymer that is tolerated by the body and reacts with the crosslinking agent to produce a prepolymer macromolecular crosslinking product. The prepolymer product is one that is a reaction product between the crosslinking agent and the polymer, and includes a polymer backbone with one or more crosslinking molecules covalently bonded thereto such that the polymer backbone includes one or more crosslinking functional groups, where the crosslinking functional groups include at least one reactive moiety, e.g., an aldehyde moiety, that can covalently bond to the protein component of the proteinaceous substrate. As such, the prepolymer product retains the ability to crosslink upon contact with the proteinaceous substrate. The prepolymer product of certain embodiments is a soluble macromolecule that comprises a polymeric backbone molecule bound to crosslinking agent molecules, where at least a portion of the bound crosslinking agent molecules retain a free crosslinking moiety that can bind proteins in the proteinaceous substrate. This prepolymer product "macromolecular" crosslinking agent may vary in average molecular weight, and in certain embodiments may range in weight from 10,000 to 4 million Daltons, such as 500,000 to 2 million Daltons.

In certain embodiments, the physiologically acceptable polymer is a glycosaminoglycan (i.e., a mucopolysaccharide). Specific glycosaminoglycans of interest include, but are not limited to: chondroitin sulphate; dermatan sulphate; keratan sulphate; heparin; heparan sulphate; and hyaluronan (i.e., hyaluronic acid). In certain embodiments, the glycosaminoglycan component is hyaluronan.

The crosslinking agent is present in the crosslinking composition in excess with respect to the amount of physiologically acceptable polymer. In certain embodiments, the amount of physiologically acceptable polymer makes up from 0.01 to 5% (w/v), such as 0.05 to 3% (w/v) including 0.1 to 1% (w/v) of the crosslinking composition.

In certain embodiments, the crosslinker composition may further include an amount of a viscosity modifying agent. Viscosity modifying agents of interest include, but are not limited to: polyoxyethylene or polyoxypropylene polymers or copolymers thereof, such as polyethylene glycol and polypropylene glycol; nonionic cellulose ethers such as methylcellulose, ethylcellulose, hydroxymethylcellulose, hydroxyethylcellulose, carboxymethylcellulose, carboxyethylcellulose and hydroxypropylcellulose; additional celluloses, such as carboxymethylcellulose sodium, carboxymethylcellulose calcium, carboxymethylstarch; and the like. In certain embodiments of particular interest, the emulsifying agent is a cellulose ether, particularly a nonionic cellulose ether, such as carboxymethylcellulose. Carboxymethylcellulose is available from a variety of commercial sources, including but limited to, Sigma, Hercules, Fluka and Noviant. In certain embodiments, the average molecular weight of the cellulose ether is at least about 1000 Daltons, such as at least about 5000 Daltons, where the average molecular weight may be as high as 10,000 Daltons or higher, e.g., 50,000 Daltons or higher, 100,000 Daltons or higher, and ranges in certain embodiments from about 5,000 to about 100,000 Daltons, such as from about 10,000 to about 50,000 Daltons. The proportion of the viscosity modifying agent in the sealant in certain embodiments ranges from 0.01 to 10% (v/v), such as 0.1 to 4% (v/v) including 0.5 to 2% (v/v).

Proteinaceous Substrate

The liquid proteinaceous substrate from which the subject phase invertible compositions are prepared is a liquid composition, e.g., an aqueous composition, that is made up of at least a proteinaceous component and, in certain embodiments, an adhesion modifier, where the substrate may include one or more additional components, including, but not limited to: a plasticizer; a carbohydrate; and the like.

The substrate may be sterilized according to any convenient protocol, where sterilization protocols of interest include, but are not limited to: gamma radiation, electron beam and the like.

The liquid proteinaceous substrate is one that is storage stable. By storage stable is meant that the substrate may be maintained under storage conditions, such as room temperature for a period of time of at least 1 years or longer, such as 3 years or longer, without undergoing any substantial change that negatively impacts the function of the substrate such that it is no longer suitable for use in preparing a biocompatible phase invertible composition of the invention.

Proteinaceous Component

The proteinaceous component (i.e., proteinaceous material) of the substrate is made up of one or more distinct proteins. The proteins of this component may be either synthetic or naturally occurring proteins, where the proteins may be obtained/prepared using any convenient protocol, e.g., purification from naturally occurring sources, recombinant production, synthetic production, and the like, where in certain embodiments the proteins are obtained from naturally occurring, e.g., bovine, porcine or human, sources. Specific proteins of interest include, but are not limited to: albumins, collagens, elastins, fibrins, and the like.

The amount of protein in the substrate composition may vary, where the specific selection of concentration is dependent on the desired application and product parameters desired therefore, such as tenacity, hardness, elasticity, resorption characteristics and platelet aggregation effects. In certain embodiments, the total protein total concentration in the substrate compositions ranges from about 1 to 75% (w/w), such as 1-50% (w/w), including 5 to 40% (w/w).

In certain embodiments, the primary protein of the substrate composition of this embodiment is albumin, where the albumin may be a naturally occurring albumin, e.g., human albumin, bovine albumin, porcine albumin etc., or a variant thereof. As is known in the art, the albumin may be purchased in powdered form and then solubilized into an aqueous suspension, or alternately, may be purchased in aqueous form. Purified albumin may derived from any one of a number of different sources including, bovine, ovine, equine, human, or avian in accordance to well known methods (ref.: Cohn et. al, J. Amer. Chem. Soc. 69:1753) or may be purchased in purified form from a supplier, such as Aldrich Chemical (St. Louis, Mo.), in lyophilized or aqueous form. The albumin may be derivatized to act as a carrier for drugs, such as heparin sulfate, growth factors, antibiotics, or may be modified in an effort to moderate viscosity, or hydrophilicity. Derivatization using acetylating agents, such as, but not limited to, succinic anhydride, and lauryl chlorides, are useful for the production of binding sites for the addition of useful molecules. In these embodiments where the proteinaceous component includes albumin, the albumin may be present in concentrations ranging from about 10 to about 50% (w/w), such as from about 30 to about 40% (w/w).

In certain embodiments, the proteinaceous component also includes a collagen, e.g., a naturally occurring collagen (human, bovine, porcine) or synthetic variant thereof. In accordance with the invention, the collagen may be in dry or aqueous forms when mixed with the albumin. Collagen may be derivatized to increase it utility. Acylating agents, such as anhydrides or acid chlorides, have been found to produce useful sites for binding of molecules such as growth factors, and antibiotics. When present, the collagen sometimes ranges from about 1 to about 20% (w/w), including from about 1 to about 10% (w/w), such as from about 1 to about 4% (w/w), including from about 2 to 4% (w/w).

The subject proteinaceous component, as described above, may or may not include one or more active agents, e.g., drugs, present in it, as desired. When present, the agent(s) may be bound to the polymers, as desired.

Tackifying Agent

Also present may be one or more tackifying agents. Tackifying agents improve the adhesiveness of the sealant to the biological surface. In many embodiments, the adhesion modifiers are polymeric compounds having charged functionalities, e.g., amines, etc. Whereas numerous tackifying agents may be used, one of particular applicability is polyethyleneimine (PEI). PEI is a long chain branched, alkyl polymer containing primary, secondary and tertiary amines. The presence of these highly ionic groups results in significant attachment through ionic interactions with the underlying surface. In addition, the presence of PEI in the substrate significantly enhances the presence of amine terminals suitable to produce crosslinks with the crosslinking agent. Additional tacking agents of interest include, but are not limited to: gelatin, carboxymethylcellulose, butylhydroxytoluene, chitosan, etc.

In certain embodiments of the invention, tackifying agents are used to modify adhesion to the biological substrate while simultaneously creating a procoagulant. In certain embodiments, the tacking agents are present in concentrations of from about 0.1 to about 10% (w/w), such as from about 0.1 to about 4% (w/w).

Optional Components

The above described substrate component of the subject compositions may, in certain embodiments, include one or more optional components that modify the properties of the phase invertible composition produced from the substrate and crosslinker. Representative optional components of interest are now discussed in greater detail below.

Plasticizing Agents

In accordance to the invention, a plasticizing agent may be present in the substrate. The plasticizing agent provides a number of functions, including wetting of a surface, or alternately, increasing the elastic modulus of the material, or further still, aiding in the mixing and application of the material. Numerous plasticizing agents exist, including fatty acids, e.g., oleic acid, palmitic acid, etc., dioctylphtalate, phospholipids, and phosphatidic acid. Because plasticizers are typically water insoluble organic substances and are not readily miscible with water, it is sometimes advantageous to modify their miscibility with water, by pre-mixing the appropriate plasticizer with an alcohol to reduce the surface tension associated with the solution. To this end, any alcohol may be used. In one representative embodiment of this invention, oleic acid is mixed with ethanol to form a 50% (w/w) solution and this solution then is used to plasticize the proteinaceous substrate during the formulation process. Whereas the type and concentration of the plasticizing agent is dependent upon the application, in certain embodiments the final concentration of the plasticizing agent is from about 0.01 to 10% (w/w), including from about 2 to about 4% (w/w). Other plasticizing agents of interest include, but are not limited to: polyethylene glycol, glycerine, butylhydroxytoluene, etc.

Carbohydrate Procoagulant

In certain embodiments, the substrates include a carbohydrate procoagulant. Chitosan and derivates of chitosan are potent coagulators of blood and, therefore, are beneficial in formulating sealant materials capable of sealing vascular injuries. While virtually all chitin materials have been demonstrated to have some procoagulant activity, in accordance to the invention, the use of acetylated chitin is employed as an additive for the formulation of sealant intended for blood control. Acetylation of the molecule can be achieved in a number of different ways, but one common method is the treatment of chitosan/acetic acid mixtures with acid anhydrides, such as succinic. This reaction is readily carried out at room temperature. In accordance with the invention, gels created in this manner combined with proteinaceous substrates and crosslinked in situ are beneficial for the creation of a biocomposite structural member. As such, the carbohydrate procoagulant may be chitosan, low molecular weight chitosan, chitin, chitosan oligosaccharides, and chitosan derivatives thereof. In accordance with the teachings of this invention the carbohydrate component, e.g., chitosan, may be present in concentrations ranging from about 0 to about 20%, such as from about 0.1 to about 5% (w/w).

Fillers

Fillers of interest include both reinforcing and non-reinforcing fillers. Reinforcing fillers may be included, such as chopped fibrous silk, polyester, PTFE, NYLON, carbon fibers, polypropylene, polyurethane, glass, etc. Fibers can be modified, e.g., as described above for the other components, as desired, e.g., to increase wettability, mixability, etc. Reinforcing fillers may be present from about 0 to 40%, such as from about 10 to about 30%. Non-reinforcing fillers may also be included, e.g., clay, mica, hydroxyapatite, calcium sulfate, bone chips, etc. Where desired, these fillers may also be modified, e.g., as described above. Non-reinforcing fillers may be present from about 0 to 40%, such as from about 10 to about 30%.

Biologically Active Agents

Biologically active agents may be included, e.g., bone growth factors, tissue activators, cartilage growth activators, small molecule active agents, etc. Thus, the biologically active agents can include peptides, polypeptides, proteins, saccharides, polysaccharides and carbohydrates, nucleic acids, and small molecule organic and inorganic materials. Specific biologically active agents include antibiotics, antivirals, steroidal and non-steroidal anti-inflammatories, antineoplastics, anti-spasmodics including channel blockers, modulators of cell-extracellular matrix interactions including cell growth inhibitors and anti-adhesion molecules, enzymes and enzyme inhibitors, anticoagulants, growth factors, DNA, RNA and protein synthesis inhibitors, anti-cell migratory agents, vasodilators, and other drugs used for treatment of injury to tissue. Examples of these compounds include angiotensin converting enzyme inhibitors, antithrombotic agents, prostacyclin, heparin, salicylates, thrombocytic agents, anti-proliferative agents, nitrates, calcium channel blocking drugs, streptokinase, urokinase, tissue plasminogen activator (TPA) and anisoylated plasminogen activator (PA) and anisoylated plasminogen-streptokinase activator complex (APSAC), colchicine and alkylating agents, growth modulating factors such as interleukins, transformation growth factor P and congeners of platelet derived growth factor, monoclonal antibodies directed against growth factors, modified extracellular matrix components or their receptors, lipid and cholesterol sequestrants and other agents which may modulate vessel tone, function, arteriosclerosis, and the healing response to vessel or organ injury post intervention.

Foaming Agent

In certain embodiments, the substrate may include a foaming agent which, upon combination with the crosslinker composition, results in a foaming composition, e.g., a composition that includes gaseous airbubbles interspersed about. Any convenient foaming agent may be present, where the foaming agent may be an agent that, upon contact with the crosslinking composition, produces a gas that provides bubble generation and, hence, the desired foaming characteristics of the composition. For example, a salt such as sodium bicarbonate in an amount ranging from about 2 to about 5% w/w may be present in the substrate. Upon combination of the substrate with an acidic crosslinker composition, e.g., having a pH of about 5, a foaming composition is produced.

Additional Modifiers

Additional modifiers may also be present. For example, blends of one or more polymers (e.g., polyblends), such as Teflon, PET, NYLON, hydrogels, polypropylene, etc., may be present. The polyblends may be modified, e.g., as described above, to provide for desired properties. These additional modifiers may be present in amounts ranging from about 0 to 50%, including from about 10 to about 30%.

Buffer

Upon mixture of the proteinaceous substrate and crosslinker to produce the subject phase invertible composition, buffering of the phase invertible composition is employed in certain embodiments for a number of reasons, e.g., to optimize the bonding strength of the composition to the attaching surface, to optimize the conditions necessary for internal crosslinking to occur, etc. For example, optimum crosslinking for proteins using glutaraldehyde crosslinkers occurs at pH range from about 6 to about 8. Buffers capable of maintaining this range are useful in this invention, as long as they do not interfere with the carbonyl terminal of the crosslinker or modify the amine terminus of the amino acids. For example, phosphate buffers have a pKa value in the range of pH 7.0 and do not interfere with the crosslinking process because they do not contain carboxylic or amine functionalities. Phosphate buffer up to 1 M in strength is suitable for use as a buffer in the present invention, where in certain embodiments the phosphate buffer is about 0.01 to about 0.3M in strength. While phosphate buffering of the solutions is ideal for the stability of the protein substrate in applications where increased adhesion is required, an acidic buffer may be used as well. Citrate buffers 0.1-1 M and having a pH range of about 4.5 to about 6.5 have been found to be useful for this invention.

The buffer may be present in either the initial crosslinker component or the initial proteinaceous substrate component, or present in both components, as desired.

Combination of Substrate and Crosslinker to Produce Phase Invertible Composition As summarized above, the subject phase invertible compositions are prepared by combining a liquid proteinaceous substrate and a liquid crosslinker in appropriate amounts and under conditions sufficient for the phase invertible composition to be produced. In certain embodiments, the substrate and crosslinker are combined in a ratio (v/v) ranging from about 1/5 to about 5/1; so that a resultant phase invertible composition is produced in which the total protein concentration ranges from about 10 to about 60%, such as from about 20 to about 50%, including from about 30 to about 40% and the total crosslinker composition ranges from about 0.1 to about 20%, such as from about 0.5 to about 15%, including from about 1 to about 10%.

Combination of the substrate and crosslinker typically occurs under mixing conditions, such that the two liquid components are thoroughly combined or mixed with each other. Combination or mixing may be carried out using any convenient protocol, e.g., by manually combining two components, by employing a device that combines the two components, etc. Combination or mixing is typically carried out at a temperature ranging from about 20 to about 40° C., such as room temperature.

Combination of the proteinaceous substrate and crosslinker as described above results in the production of a phase invertible composition. By phase invertible composition is meant a composition that goes from a first liquid state to a second non-fluid, e.g., gel or solid, state. In the second non-fluid state, the composition is substantially, if not completely, incapable of fluid flow. The phase invertible composition typically remains in a fluid state, following combination of the substrate and crosslinker components, for a period of time ranging from about 10 seconds to about 10 minutes, such as from about 20 seconds to about 5 minutes, including from about 30 seconds to about 120 second, when maintained at a temperature ranging from about 15° C. to about 40° C., such as from about 20° C. to about 30° C.

Specific phase invertible formulations include as components: (i) a first composition comprising a proteinaceous substrate composition having about 30%-50% albumin, and about 0.1%-0.3% chitosan chloride; and (ii) a second composition comprising a crosslinking composition having about 3%-10% heat treated glutaraldehyde, about 0.1%-1% hyaluronic acid, and optionally, about 0%-1.5% sodium salt of carboxymethylcellulose high viscosity. Such phase invertible formulations generally have an average cure time of about 5-60 seconds upon admixing of the first and second compositions, and an average burst of about 125-1000 mmHg, and more typically, an average cure time of about 10-30 seconds, and an average burst of about 200-850 mmHg, as measured at about room temperature.

In a particular embodiment, a phase invertible formulation is provided that includes as components: (i) a first composition comprising a proteinaceous substrate composition having about 40% albumin, and about 0.2% chitosan chloride; and (ii) a second composition comprising a cross-linking composition having about 4.4%-7.5% heat treated glutaraldehyde, about 0.2% hyaluronic acid, and optionally, about 0%-0.75% sodium salt of carboxymethylcellulose high viscosity. Such phase invertible formulations generally have an average cure time of about 10-30 seconds upon admixing of the first and second compositions, and an average burst of about 250-800 mmHg, and more typically, an average cure time of about 10-25 seconds, and an average burst of about 350-700 mmHg, as measured at about room temperature.

As also described above, various additional materials can be incorporated into the phase invertible compositions to serve any of several purposes, such as to modify the physical characteristics of the composition, and/or aid in the repair of a target tissue or biological material to which the composition is applied. For example, biologically active agents such as peptides, proteins, nucleic acids, carbohydrate molecules, small molecules and the like can be incorporated to attract and bind specific cell types, such as white cells and platelets, or materials such as fibronectin, vimentin, and collagen, can be used to enhance healing by non-specific binding.

Tracing material, such as barium, iodine or tantalum salts, may also be included to allow visualization and/or monitoring of the phase invertible composition. In certain embodiments, different biologically active agents can be used in different applications or layers when one or more phase invertible compositions is differentially applied.

In certain embodiments, cells can also be incorporated into or applied in connection with the phase invertible compositions before, during and/or after application of the composition. When employed, cells are generally included in the proteinaceous substrate composition, or applied in conjunction with or separately from the phase invertible composition in a manner that allows their adherence at the site of application. The cells can be living, artificial cells, cell ghosts (i.e., red blood cell or platelet ghosts), or pseudovirions, depending on a given end use.

For example, the cells may be selected to produce specific agents such as growth factors at the site of application. Biologically active agents that modulate cell viability, differentiation, and/or growth can be included as well. In some embodiments, the cells may be stem cells, or in other embodiments, progenitor cells corresponding to the type of tissue at the treatment location or other cells, providing therapeutic advantages. For example, liver cells incorporated into the phase invertible composition and applied to a wound or surface of the liver of a patient may aid in its regeneration and repair. This may be particular useful in cases where diseases such as cirrhosis, fibrosis, cystic disease or malignancy results in non-functional tissue, scar formation or tissue replacement with cancerous cells. Similar methods may be applied to other organs and tissues as well.

The biologically active agents can be incorporated physically and/or by chemical attachment. Physical incorporation is carried out by mixing the biologically active agent with the phase invertible material prior to and/or during application to the target surface and curing. The material is usually mixed into the proteinaceous substrate solution to form a solution, suspension or dispersion. In one embodiment, the biologically active agent can be encapsulated within delivery devices such as microspheres, microcapsules, liposomes, cell ghosts or pseudovirions, which in themselves effect release rates and uptake by cells. Chemical incorporation of the biologically active agent is carried out by chemically coupling the agent to a polymeric material of either the proteinaceous substrate or crosslinking composition, usually the proteinaceous substrate, before or at the time of polymerization (e.g., by conjugation through reactive functional groups, such as amines, hydroxyls, thiols, and the like). To ensure that the desired cure times and burst properties of the phase invertible composition are maintained, physical and/or chemical incorporation of a biologically active agent takes into consideration the relative amounts of proteinaceous substrate and crosslinker present in the final composition, and can be adjusted accordingly.

Methods

The subject biocompatible phase invertible compositions are employed in methods where a quantity of the phase invertible composition is delivered to a particular site or location of a subject, patient or host in need thereof. The subject, patient or host is typically a "mammal" or "mammalian," where these terms are used broadly to describe organisms which are within the class mammalian, including, but not limited to, the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the animals or hosts, i.e., subjects (also referred to herein as patients) will be humans.

The quantity that is delivered to the subject in any given application will necessarily vary depending on the nature of the application and use of the composition, but in certain representative embodiments ranges from about 1 to about 50 ml, such as from about 1 to about 25 ml, including from about 1 to about 5 ml, e.g., about 3 ml.

While necessarily dependent on the particular application in which the subject composition is being employed, the subject composition is, in many embodiments, locally delivered to a particular region, site or location of the host, where the site or location may, of course, vary. Representative sites or locations include, but are not limited to: vessels, organs, and the like. Depending on the particular application, the composition may be delivered to the site of interest manually or with a delivery device, e.g., the delivery device employed to deliver the composition in stenting applications, described in greater detail below.

Utility

The subject biocompatible phase invertible compositions find use in a variety of different applications. Representative applications of the subject phase invertible compositions include those described in U.S. Pat. Nos. 3,438,374; 5,092, 841; 5,292,362; 5,385,606; 5,575,815; 5,583,114; 5,843, 156; 6,162,241; 6,290,729; 6,302,898; 6,310,036; 6,329, 337; 6,371,975; 6,372,229; 6,423,333; 6,458,147; 6,475, 182; 6,547,806; and 7,303,757; as well as U.S. Application Nos. 2002/0015724; 2002/0022588; 2002/0133193; 2002/ 0173770; 2002/0183244; 2002/019490; 2002/0032143; the disclosures of which are herein incorporated by reference.

Systems

Also provided are systems for use in practicing the subject methods. The systems may include fluid delivery elements for delivery of the substrate and crosslinking composition to the site of administration, mixing elements, etc. Examples of such systems include those described in U.S. Pat. No. 7,303,757; the disclosure of which is herein incorporated by reference.

Kits

Also provided are kits for use in practicing the subject methods, where the kits typically include a distinct liquid substrate and liquid crosslinking composition components of a phase invertible fluid composition, as described above. The substrate and crosslinking compositions may be present in separate containers in the kit, e.g., where the substrate is present in a first container and the crosslinking agent is present in a second container, where the containers may or may not be present in a combined configuration.

The subject kits may also include a mixing device, for mixing the substrate and crosslinker together to produce the phase invertible composition. The kits may also include a delivery device (which may or may not include a mixing element), such as a dual barrel syringe, catheter devices, and the like, as described above.

The kit may further include other components, e.g., guidewires, sensor wires, etc., which may find use in practicing the subject methods.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are provided by way of illustration and not by way of limitation.

Experimental

Various formulations of phase invertible compositions were prepared in which the sodium salt of hyaluronic acid (HA) was included in the protein component and the cross-linking component. Illustrative formulations were tested as shown in Table 1.

TABLE 1

| Lot # | Protein Formulation | | | Crosslink Formulation | | |
|---|---|---|---|---|---|---|
| | Alb | HA | Chit Cl 213 | HTGA | HA | CMC High Vis |
| 004-49 | 40% | 0.0 % | 0.2% | 7.5% | 0.2% | 0.00% |
| 004-42-1 | 40% | 0.2% | 0.2% | 4.4% | 0.0% | 0.75% |
| 004-42-2 | 40% | 0.2% | 0.2% | 7.5% | 0.0% | 0.75% |
| 004-42-3 | 40% | 0.2% | 0.2% | 4.4% | 0.0% | 0.00% |
| 003-118-2 | 40% | 0.0% | 0.2% | 7.5% | 0.2% | 0.75% |

Abbreviations: Alb = Albumin;
HA = Hyaluronic acid;
Chit Cl 213 = Chitosan Chloride;
HTGA = heat treated glutaraldehyde; and
CMC High Vis = the sodium salt of carboxymethylcellulose high viscosity The protein solution is prepared in a 10 mM, pH 6.2 phosphate buffer solution. The cross-linker solution is prepared in a 10 mM, pH 7 phosphate buffer solution.

An in-vitro test system was used to determine the burst strength of each formulation. A one inch square piece of porcine aorta wall is fastened to a pressure vessel over a 5 mm diameter hole. A hole is punctured through the aorta using a 14 gauge needle. The sealant is applied to the aorta over the 14 ga needle hole and allowed to cure. Air pressure is applied to the inside of the pressure vessel until the sealant ruptures. The air pressure required to cause rupture is measured using a manometer.

TABLE 2

| Lot# | Average Cure Time (sec) n = 2 | Average Burst (mmHg) n = 2 |
|---|---|---|
| 004-49 | 19.50 | 565.20 |
| 004-42-1 | 22.00 | 353.70 |
| 004-42-2 | 13.50 | 566.20 |
| 004-42-3 | 33.50 | 246.20 |
| 003-118-2 | 11.50 | 499.20 |

The observed properties of these formulations are shown in Tabular form in FIG. 201, and in Table 2, for the aorta test system.

The results in FIG. 1 and Table 2 demonstrate that when hyaluronic acid (HA) is provided in the crosslinking component and not the protein component, undesirable interactions with the protein component are eliminated and the viscosity of the crosslinking component is enhanced, which results in an improved overall 2 component sealant composition.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a phase invertible composition, said method comprising:
    combining:
    (a) a liquid proteinaceous substrate; and
    (b) a liquid crosslinking composition comprising a macromolecular crosslinking agent which comprises a reaction product of an excess of a liquid aldehyde crosslinking agent and a glycosaminoglycan, wherein the liquid crosslinking composition has been formed prior to combining with the liquid proteinaceous substrate to produce said phase invertible composition;
    wherein said phase invertible composition is exposed to radiation.

2. The method according to claim 1, wherein the radiation sterilizes the phase invertible composition.

3. The method according to claim 1, wherein the radiation is gamma radiation.

4. The method according to claim 1, wherein the radiation is electron beam radiation.

5. The method according to claim 1, wherein said glycosaminoglycan is hyaluronan.

6. The method according to claim 1, wherein said proteinaceous substrate comprises a proteinaceous material selected from the group consisting of: albumin, elastin, fibrin and soluble and insoluble forms of collagen and combinations thereof.

7. The method according to claim 6, wherein said liquid aldehyde crosslinking agent comprises glutaraldehyde.

8. The method according to claim 7, wherein said glutaraldehyde is heat stabilized.

9. A method of producing a phase invertible composition, said method comprising:
    combining:
    (a) a liquid proteinaceous substrate; and
    (b) a liquid crosslinking composition comprising a macromolecular crosslinking agent which comprises a reaction product of an excess of a liquid aldehyde crosslinking agent and hyaluronic acid, wherein the liquid crosslinking composition has been formed prior to combining with the liquid proteinaceous substrate to produce said phase invertible composition;
    wherein said phase invertible composition is exposed to radiation.

* * * * *